United States Patent [19]

Kawaguchi et al.

[11] Patent Number: 5,151,362
[45] Date of Patent: Sep. 29, 1992

[54] APPARATUS CONTAINING A SEPTUM WHICH IMPEDES CELL PERMEATION FOR CELL CULTURE AND METHOD OF USE

[75] Inventors: Hideo Kawaguchi, Hachioji; Kouji Takeuchi, Nagareyama; Tadashi Ishibashi, Kumagaya; Norio Shimizu, Sayama; Yoji Odawara, Kodaira, all of Japan

[73] Assignee: Hitachi, Ltd., Tokyo, Japan

[21] Appl. No.: 505,326

[22] Filed: Apr. 5, 1990

[30] Foreign Application Priority Data

Aug. 25, 1989 [JP] Japan .................. 1-217338

[51] Int. Cl.$^5$ .................. C12N 5/02; C12M 3/02; C12M 1/12
[52] U.S. Cl. .................. 435/240.25; 435/284; 435/286; 435/311; 435/813
[58] Field of Search .............. 435/813, 311, 173, 284, 435/286, 240.1, 240.25, 819, 287; 210/748

[56] References Cited

U.S. PATENT DOCUMENTS

| | | | |
|---|---|---|---|
| 3,743,582 | 7/1973 | Atsuo et al. | 435/813 |
| 4,016,044 | 4/1977 | Fresnel et al. | 435/813 |
| 4,218,538 | 8/1980 | Church | 435/813 |
| 4,251,633 | 2/1981 | Orlowski et al. | 435/813 |
| 4,440,638 | 4/1984 | Judy et al. | 210/748 |
| 4,535,062 | 8/1985 | Müller | 435/311 |
| 4,568,643 | 2/1986 | Levy | 455/813 |
| 4,861,725 | 8/1989 | Liau | 435/311 |

OTHER PUBLICATIONS

Katsuta et al., In Vitro, 15(12) pp. 949-956 (1979).

Primary Examiner—Jill A. Johnston
Assistant Examiner—William Chan
Attorney, Agent, or Firm—Pennie & Edmonds

[57] ABSTRACT

By culturing cells in an apparatus containing a first zone in which a cell suspended medium is present and a second zone in which liquid containing a physiological saline solution and/or nutrient sources is present, the first zone being separated from the second zone by a septum with characteristics, such as pores size or electrostatic charges, which impedes the cells from freely permeating through, while allowing at least one of nutrient sources, cell wastes or the product to move between the first zone and the second zone via the septum to proliferate cells in the first zone, wherein a flow rate via the septum is controlled in such a manner that the cell count moved from the first zone into the second zone via the septum does not exceed the cell count increased by cell growth in the first zone. Thus, cell culture at a high cell density can be achieved in a large scale.

15 Claims, 7 Drawing Sheets

APPARATUS CONTAINING A SEPTUM WHICH IMPEDES CELL PERMEATION FOR CELL CULTURE AND METHOD OF USE

BACKGROUND OF THE INVENTION

1. Field of the Invention

The present invention relates to cell culture, and more particularly to a process for cell culture which achieves cell growth at a high cell density in a suspended state and is suitable for large-scale processing as well as for a culturing apparatus for the process.

2. Related Art Statement

Culture of mammalian cells in a large scale is an important technique for means of producing physiologically active substances used for medical drugs, diagnostics, etc.

Mammalian cells are roughly classified into those that can be proliferated in a suspended state and those that can grow only in a state adhered to a solid surface. As suspension culture apparatuses for the former case, there are employed a spinner flask, a roller bottle, a mechanical stirring type culture tank, etc. In the culture using apparatuses described above, however, cells are cultured in a fixed amount of nutrient sources so that a cell density of about $1 \times 10^6$ cells/ml is obtained in many cell systems. As a method for culturing cells to a higher cell density level, there is known a method which comprises aseptically separating and collecting the cultured cells from the medium by means of centrifugation, etc., and resuspending and culturing the cells in a fresh medium. That is, cell wastes exhausted from cells and accumulated in a medium are withdrawn and a fresh medium is supplemented to supply nutrient sources; by doing so, a high cell density can be obtained. However, repeated centrifugation or the like permits various bacteria to readily invade into the culture system and its operations become complicated. Accordingly, it is desirable to continuously supply the culture system with nutrient sources and remove cell wastes from the culture system.

In order to realize this continuous supply of nutrient sources and removal of cell wastes, it is necessary to isolate cells stably over a long period of time without any cell damage. In recent years, some methods for high cell density cell culture in a large scale have been proposed to continuously supply nutrient sources and remove cell wastes.

For example, there are provided a method for exchanging a medium through filtration by rotating a cylindrical filter having the surface parallel to coaxial rotation while preventing the filter from getting clogged, and an apparatus suitable for the method (U.S. Pat. No. 3,647,632). There are also provided a method which comprises providing a pipe with an opening toward the bottom of a culture tank for precipitating cells in the tank and supplementing a fresh medium while exhausting out of the culture tank the supernatant obtained as the result of precipitation of the cells, and an apparatus for the method (Japanese Patent Application KOKOKU No. 61-36915). Furthermore, there are known a method for culturing cells which comprises using a semi-permeable membrane having permeability specific to selected nutrients, cell wastes or gas, passing a cell-containing medium and a cell-free medium along both sides of the semi-permeable membrane described above parallel to the membrane and supplying or discharging nutrients, cell wastes or gas into or from the cell-containing medium, and an apparatus used therefor (Japanese Patent Application KOKOKU No. 59-175877 and Japanese Patent Application KOKOKU NO. 59-175878).

According to the method for cell isolation using a filter, however, the filter tends to get easily clogged when used over long periods of time and any device is thus required to prevent the clogging; but the problem has not yet been satisfactorily overcome on an industrial level. Furthermore, the method using a precipitation tube involves a problem of cell damage due to oxygen starvation since cells settle in the precipitation tube for a long time. Further in the method using a semi-permeable membrane having permeability specific to the selected nutrient, cell wastes or gas, molecules are selectively permeated so that a pore diameter of the membrane is very small and a diffusion rate of nutrient or cell wastes through the membrane is small. Accordingly, it is difficult to obtain sufficient diffusion amounts of these substances at high density culture in a large scale. The semi-permeable membrane described above is also poor in mechanical strength and is thus unsuitable for culture over long periods of time.

SUMMARY OF THE INVENTION

An object of the present invention is to provide a process for cell culture suitable for high cell density in a large scale which can stably supply nutrient sources over long periods of time, can remove cell wastes and can effect cell growth in a suspended state, without inflicting trauma on the cells. Another object of the present invention is to provide an apparatus suitable for such a process.

A first aspect of the invention is directed to a process for cell culture which comprises culturing cells in an apparatus comprising a first zone in which a cell suspended medium is present and a second zone in which liquid containing a physiological saline solution and/or nutrient sources is present, said first zone being separated from said second zone by a septum with pores having a diameter sufficient to permit cells to permeate therethrough, while allowing at least one of nutrient sources, cell wastes or the product to move between the first zone and the second zone via the septum to proliferate cells in the first zone.

A second aspect of the invention is directed to a cell culture apparatus comprising a culture tank equipped with a septum with pores having a diameter sufficient to permit cells to permeate therethrough, the culture tank comprising a first zone in which a cell suspended medium is present and a second zone in which liquid containing a physiological saline solution and/or nutrient sources is present, said first zone being separated from said second zone by said septum, and a means for moving at least one of nutrient sources, cell wastes or the product between the first zone and the second zone via the septum.

The characteristic feature of the present invention lies in performing cell culture using a membrane having pores large enough to be able to permeate cells therethrough, in place of a semi-permeable membrane having a small pore size heretofore used in conventional cell culture. That is, the present invention has been achieved based on the finding that cells are cultured in an apparatus in which the first zone for culturing cells is separated from the second zone in which liquid containing nutrient sources and/or a physiological saline solution is present, so that cell wastes exhausted from cells which prevents cell growth is easily moved from the first zone into the second zone and the nutrient sources in the second zone are easily moved into the first zone, whereby cell growth is markedly accelerated.

DETAILED DESCRIPTION OF THE INVENTION

Figure 1:
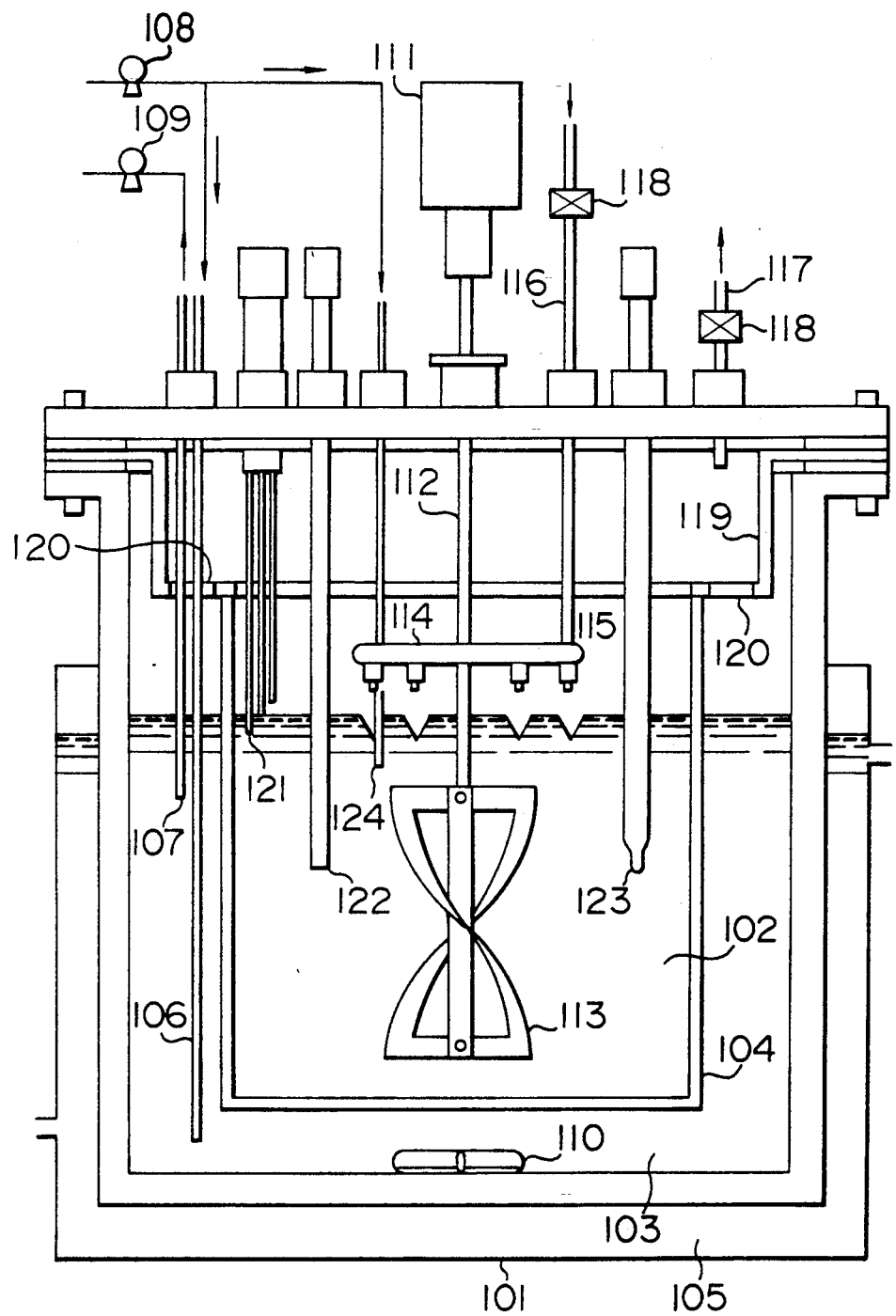
FIG. 1 shows an example of a culture tank with a cylindrical septum closed at the bottom.

The movement of nutrient sources, cell wastes or the product produced by the culture cells between the first zone and the second zone via the septum having a pore size large enough to permit cells to permeate therethrough can be achieved, for example, by adding medium to the first zone and/or the second zone and withdrawing the medium from the second zone.

At this stage, in case that the count of cells moved from the first zone into the second zone via the septum does not exceed the count of cells increased by cell growth in the first zone, the cell count in the first zone increases. However, for efficient culture, it is desirable to reduce the cell movement as much as possible. The movement of cells is effected, for example, by liquid flow via the septum. Therefore, where medium is added to the first zone, an amount of liquid flow added is controlled thereby to regulate a flow rate of medium permeated through the septum. Thus, the cell count moved from the first zone into the second zone can be reduced. Further where medium is added to the second zone, a pressure difference between the first zone and the second zone via the septum is rendered substantially zero. Thus, a liquid flow via the septum can be reduced and the cells moved from the first zone into the second zone can be decreased. In order to make the pressure difference between the first zone and the second zone substantially zero, the pressure of the gaseous phase in the first zone is made equal to that of the gaseous phase in the septum so that the substantially zero pressure difference can be realized. Where medium is added to the second zone, the movement of the substance(s) via the septum is caused mainly by diffusion. A driving force of the diffusion is a concentration difference in substance between the first zone and the second zone.

Where medium is supplemented in the first zone through the septum having pores of a size to permit cells to permeate therethrough, clogging of the septum occurs only with difficulty as compared to a septum with pores having a small size so that reverse washing used to be always necessary is hardly required in culture for several weeks. Accordingly, the construction of the apparatus becomes simple and driving operations are extremely easy. Furthermore in culture over several months, clogging may occur sometimes even though the septum with pores having a pore size for permitting cells to permeate therethrough is used. However, this clogging can be readily recovered by reverse washing in a short time by a liquid flow from the second zone into the first zone via the septum or by forced extrusion of the clogged matter in a short time by a liquid from the first zone to the second zone via the septum. For example, reverse washing can be readily performed, without using any special device, by forming a liquid flow in a short time from the second zone to the first zone via the septum, due to a hydrostatic pressure difference between the first and second zones caused by rapid addition of medium to the second zone. Furthermore, the forced extrusion operation of the clogged matter can be easily performed, without using any special device, by forming a liquid flow in a short time from the first zone to the second zone via the septum, due to a hydrostatic pressure difference between the first and second zones caused by rapidly adding medium to the first zone. In addition, when the septum with pores having a pore size for permitting cells to permeate therethrough is used, cell fragments or high molecular wastes exhausted by cells can easily permeate through the septum. Growth inhibition can thus be avoided by the fragments or wastes. Next, where medium is supplemented to the second zone separated from the first zone by the septum with pores having a pore size for permitting cells to permeate therethrough, a rate of moving substance via the septum is larger than the case of using a septum with pores having a small size, for example, a semi-permeable membrane, so that cell culture at high cell density is easily made in a large scale.

By the characteristic feature of the present invention described above, good culture conditions for cells can be easily maintained. It is also possible to provide a compact culture apparatus. Therefore, cell culture at high cell density can be carried out in a large scale.

Hereafter the present invention is concretely described with reference to the drawings.

FIG. 1 is an outlined drawing showing an example of a culture apparatus in accordance with the present invention. In FIG. 1, the apparatus is constructed by an inner tank portion 102 corresponding to the first zone for suspending cells, which is separated by a cylindrical septum 104 closed at the bottom, an outer tank 103 for permitting liquid to pass therethrough which corresponds to the second zone and a jacket 105 for recycling hot water thereby to keep the temperature of culture tank 101. By making the septum 104 into a cylindrical shape closed at the bottom, a dead zone for agitation is removed and mild conditions for agitation can be chosen.

The septum 104 is composed of a woven cloth-like material (trademark, SUS FIBER FILTER SF-05) formed into a cylinder by heat-pressing SUS316L-made fibers and has a nominal pore size of 5 μm. However, the material constructing the septum 104 is not limited to the woven cloth-like material described above but any material may be used so long as it does not inhibit cell growth. However, it is desired to use materials hard to adhere cells thereto. For example, polytetrafluoroethylene, ceramics, etc. may also be used. Furthermore, the septum 104 may also be constructed with materials having a static charge with the same polarity as that of the cells in the inner tank portion 102. When such a material is used, it is difficult for the cells to approach the septum 104 due to an electric repellency so that the cell count moved from the inner tank portion 102 to the outer tank portion 103 via the septum 104 can be reduced. As such a material, they are olefin polymer to which ionic groups are added on the main chain, and the like. Furthermore, by applying a potential having the same polarity as that of the cells in the inner tank portion 102 to the septum 104, the same effects as achieved by the electric repellency described above can be obtained. In this case, it is desired that a potential applied to the septum 104 be as weak as causing no electrolysis of liquid. In order to minimize the actual flow rate of medium in the pores as possible, it is preferred to use a septum having a large number of pores as the septum 104. More preferably, a septum composed of a woven cloth-like material or a porous material is used. It is also desired that the septum 104 has good moldability and has high mechanical strength. Then, the septum can be freely constructed to adapt for a volume or shape of the culturing apparatus. Such a septum can also withstand cell culture over long periods of time. The optimum pore size of the septum 104 can be determined according to kind of cells or property of materials for the septum.

Liquid is supplied from a medium-feeding pipe 124 to the inner tank portion 102 and/or from a medium-feeding pipe 106 to the outer tank portion 103, using a pump 108 and withdrawn from the outer tank portion 103 through a withdrawing pipe 107, using a pump 109. Flow rates of these pumps 108 and 109 can be regulated manually or by a control computer.

Using a level sensor 121, liquid flows of pumps 108 and 109 are regulated while monitoring the liquid level in the inner tank portion. Thus, the liquid level in the inner tank portion can be maintained. Where liquid is supplied to the inner tank portion 102 using the pump 108 and the liquid is withdrawn from the outer tank portion 103 using the pump 109, when the septum gets clogged and a flow rate of medium permeable through the septum becomes small, the liquid level in the inner tank portion increases. When this increase on the liquid level is detected by the level sensor 121, the pump 108 is stopped and the pump 109 is operated toward the reverse direction to rapidly supplement a fixed amount of medium to the second zone. Thus, a liquid flow generates from the second zone to the first zone via the septum due to a hydrostatic pressure difference between the first and second zones so that reverse washing of the septum can be performed. After the operation of reverse washing, the liquid is withdrawn from the outer tank portion 103 using the pump 109 to maintain the liquid level of the inner tank portion to the ordinary level. By doing so, the liquid level can be again controlled routinely using the pump 108 and the pump 109.

The liquid supplied from the medium-feeding pipe 106 may be physiological saline solution, medium, etc. It is preferred to use medium. As the liquid supplied from the medium-feeding pipe 106, fresh medium or a mixture of the medium withdrawn from the outer tank portion 103 through a withdrawing pipe 107 and fresh medium in a suitable ratio, etc. may also be used. The liquid supplied from the medium-feeding pipe 124, may be the medium. It is preferred to use medium. In addition, fresh medium or a mixture of the medium withdrawn from the outer tank portion 103 through the withdrawing pipe 107 and fresh medium in a suitable ratio, etc. may also be used.

The inner tank portion 102 is equipped with a stirring rod 112 driven by a motor 111 on the central rod and a stirring element 113 at the lower part of the stirring rod 112. Agitation of the liquid in the inner tank portion 102 is not limited only to mechanical stirring through rotation of the stirring element 113 mounted to the stirring axis 112, but stirring by blowing air into the liquid in the inner tank portion 102 may also be used. However, in the case of adding serum to the medium, it is desired to stir without foaming. In the case of using a mechanical stirrer, the a shape of the stirring element 113 is not to be particularly limited to the shape as shown in FIG. 1 but may be of any shape such as a paddle, an oar, a ribbon, etc. However, cells have a relatively weak shearing force so it is desired to use an element having a good stirring efficiency even at a low speed rotation. It is desired to set a rotation speed of the stirring axis 112 at such a speed that cells are sufficiently homogeneously dispersed.

Supply of oxygen to the medium in the inner tank portion 102 is not generally specified since a method of the supply is chosen depending upon shape of the culture tank 101, liquid amounts of the inner tank portion 102 and the outer tank portion 103, foaming property of liquid, etc. but, a ring spurger 114 may be used for example. Oxygen-containing gas is introduced from an air feeding pipe 116 into the ring spurger 114 and blown onto the liquid surface in the inner tank portion 102 through nozzles 115. Molecular oxygen from the gas-liquid interface in the dimple formed on the liquid surface moves into the medium in the inner tank portion 102. A concentration of the dissolved oxygen in the medium of the inner tank portion 102 may be controlled by varying a gas flow amount blown through the ring spurger 114, partial oxygen pressure in the gas, a rotation speed of the motor 111, etc. As other methods for supplying oxygen, there may be used upper surface aeration method in which the gas in the upper gaseous phase in the inner tank portion 102 is exchanged, a method for aeration in liquid in which porous spurgers are provided in the liquid of the inner tank portion 102 or in the outer tank portion 103 and aeration is performed through the spurgers, and the like. It is also possible to keep a pressure difference between the gaseous phase of the inner tank portion 102 and the gaseous phase of the outer tank portion 103 at substantially zero by pressure equalization ports 120 provided on a septum flange 119.

For controlling pH of the medium, there may be used, for example, a method which comprises changing a concentration of carbon dioxide in a gas blown onto the liquid surface of the inner tank portion 102 through the ring spurger 114, though the pH controlling method is not generally specified because it is chosen according to shape of the culture tank 101, volume of the medium, etc. In addition, a method of appropriately adding an alkali or an acid or the like may also be used.

The inner tank portion 102 is equipped with a level sensor 121, a dissolved oxygen concentration sensor 122, a pH sensor 123 and a temperature sensor (not shown in the drawing). A germ-free filter 118 is mounted to an air feeding pipe 116 and an air exhausting pipe 117, respectively. The germ-free filter 118 is to remove various germs in the oxygen-containing gas and to prevent various germs from invading through the air exhausting pipe 117.

Figure 2:
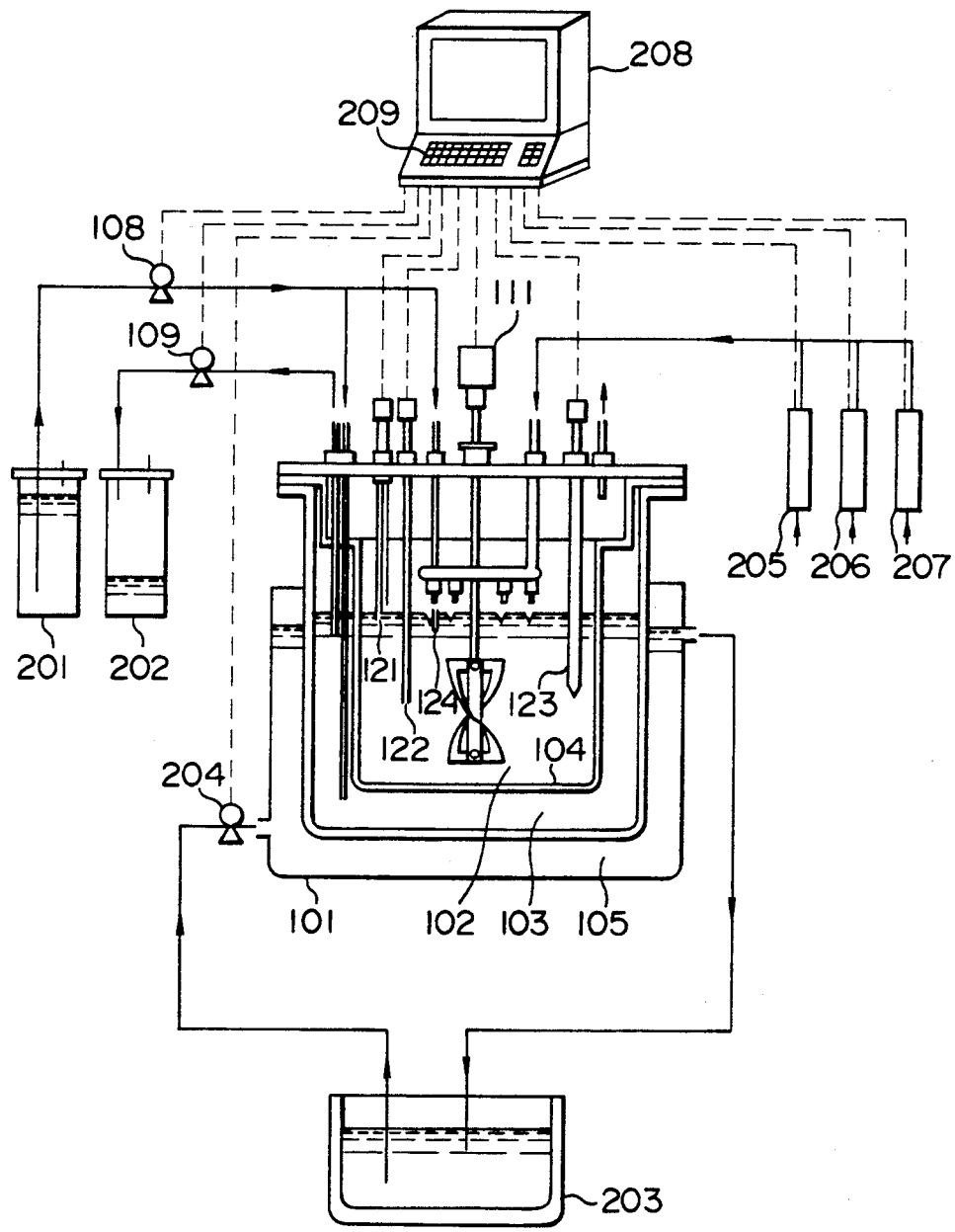
FIG. 2 shows an example of the culture system.

FIG. 2 is an outlined drawing showing an example of the culture control system in accordance with the present invention. In FIG. 2, the culture control system comprises a culturing apparatus 101, an inner tank portion 102 for suspending cells of the culturing apparatus 101 and an outer tank portion 103 which are separated from each other by a cylindrical septum 104 closed at the bottom, a tank 201 for storing liquid fed to the inner tank portion 102 and/or the outer tank portion 103, a tank 202 for storing liquid recovered from the outer tank portion 103, pump 108 for transporting liquid from the tank 201 to the inner tank portion 102 and/or the outer tank portion 103, pump 109 for transporting liquid from the outer tank portion 103 to the tank 202, a water bath with a thermostat 203, pump 204 for transporting hot water from the bath 203 to jacket 105 of the culturing apparatus 101, an air mass flow controller 205, an oxygen mass flow controller 206, a carbon dioxide mass flow controller 207, a level sensor 121 inserted into the inner tank portion 102, a dissolved oxygen concentration sensor 122, a pH sensor 123, a temperature sensor (not shown), motor 111, and a computer 208 for controlling the same.

The computer 208 for control receives data from the respective sensors 121, 122 and 123 described above and controls ON/OFF of the hot water transporting pipe 204, stepwise ON/OFF operation of the mass flow controllers 205, 206 and 207 and the rotation number of the motor 111, based on the data. The computer 208 for control also determines a flow amount of the liquid supplemented to the inner tank portion 102 and/or the outer tank portion 103, based on data such as a cell density of the medium in the inner tank portion 102, concentrations of nutrient sources and cell wastes of the liquid in the inner tank portion 102 and the outer tank portion 103, etc. and controls the liquid transporting pumps 108 and 109.

Figure 3:
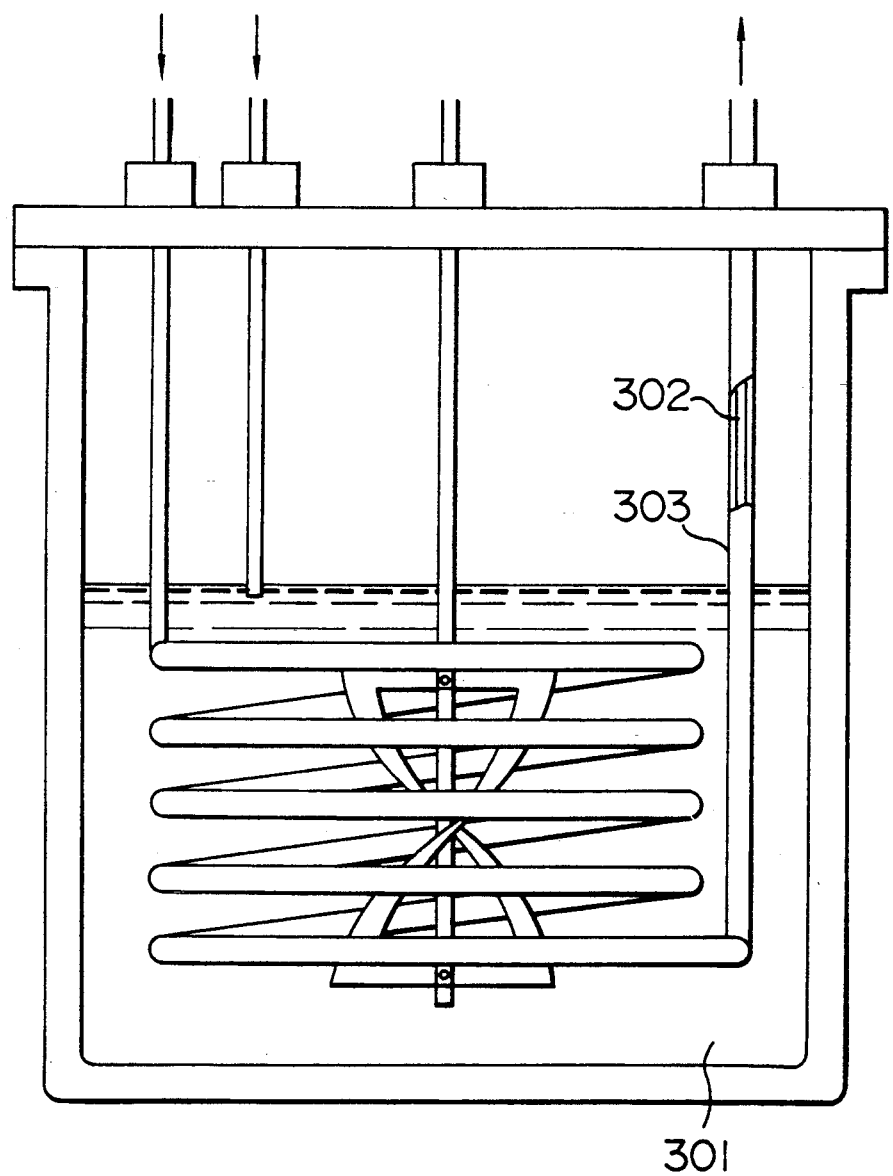
FIG. 3 shows an example of a culture tank with a tubular helical septum.

FIG. 3 is an outlined drawing showing another example of a culturing apparatus in accordance with the present invention. In FIG. 3, the apparatus comprises a culture tank portion 301 corresponding to the first zone and a tube interior 302 corresponding to the second zone. Cells are cultured in the culture tank portion 301 and liquid is passed through the tube interior 302. Septum 303 is disposed helically in the culture tank portion 301. By constructing the septum 303 as above, the surface area of the septum 303 can be increased.

Figure 4:
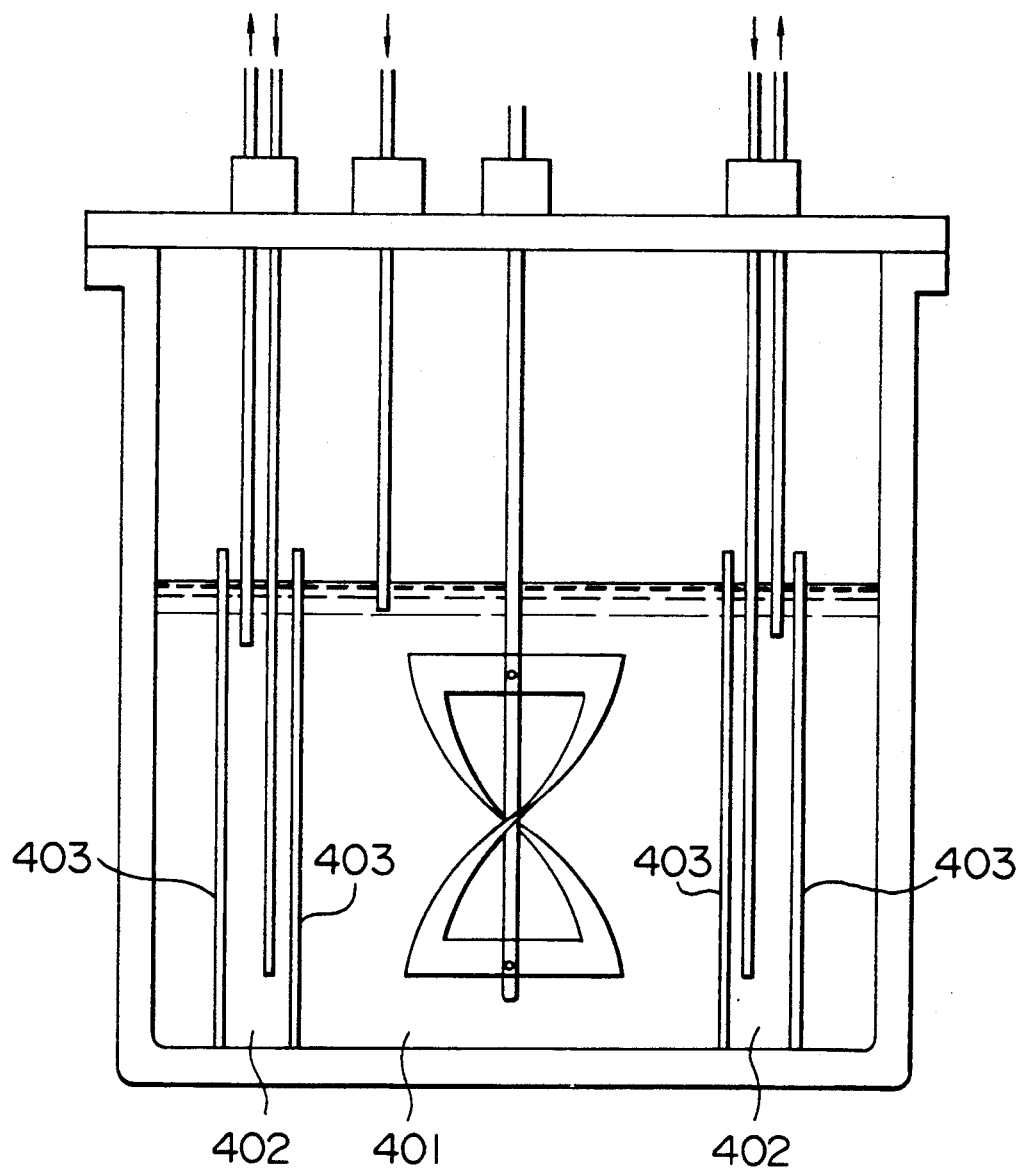
FIG. 4 shows an example of a culture tank having an outer tank portion surrounded by planar septa, the cross-section of which has a rectangular shape.

FIG. 4 is an outlined drawing showing another example of a culturing apparatus in accordance with the present invention. In FIG. 4, the apparatus comprises a culture tank portion 401 and an outer tank portion 402 which are separated by plane septa 403. Cells are cultured in the culture tank portion 401 and liquid is passed through the outer tank portion 402. The septa 403 are disposed in the culture tank portion 401 in such a combination that the cross sections in the horizontal direction form two rectangles. However, the outer tank portion 402 does not necessarily form two zones but may be one or more than 3 zones. By constructing septa 403 as above, the surface area of septa 403 can be increased.

According to the present invention, two zones are separated from each other using the septum having pores of a size large enough to permit cells to permeate therethrough and medium is continuously added preferably to the first zone and/or to the second zone thereby to remove substances which inhibit cell growth. Therefore, cell culture at high cell density can be readily achieved in a suspended state in a large scale. However, the cell count should be controlled in such a manner that the movement of cells via the septum is not too much. This is because when the cells moved from the first zone into the second zone via the septum exceeds the cell count increased by proliferation in the first zone, there occurs a so-called washout in which the cell count in the first zone decreases during incubation and cells are finally lost.

EXAMPLE 1

Using a twin tapping flask, cells were cultured.

The twin tapping flask is designed to insert a septum element between two tapping flasks used for tapping culture developed by Takaoka et al. [In Vitro, 15 (12), 949 (1979)]. By the septum element, a first tank and a second tank are separated from each other. Stirring in the tanks is effected by moving magnetic stirrer up and down with a stirrer.

A septum having an effective area of 2.1 cm$^2$ composed of SUS316L-made woven cloth-like material (manufactured by Tokyo Rope Mfg. Co., Ltd.; SUS FIBER FILTER SF-05) having a pore size of 5 $\mu$m and a thickness of 400 $\mu$m was disposed in the twin tapping flask having each volume of 200 ml. To the first tank and the second tank was added 80 ml each of DM-160AU medium (supplemented with 10% newborn bovine serum, 0.3 g/l of glutamine and 0.1 g/l of kanamycin; reinforced with 2.8 g/l of flucose). JTC-1 strain cells [Japan J. Exp. Med., 28 (2), 115–127 (1958)] were inoculated on the medium in the first tank. In this case, the cell density was $5.9 \times 10^6$ cells/ml. A rotation speed of the stirrer was set at 400 rpm and a culture temperature was set at 37° C.

The medium was added to the first tank at a flow rate of 160 ml/day and withdrawn from the second tank at a flow rate of 160 ml/day. One and two days after the inoculation, cell densities in the first tank and the second tank were measured. The results are shown in Table 1.

TABLE 1

| Tank No. | Initial Cell Density | Cell Density on Day 1 | Cell Density on Day 2 |
|---|---|---|---|
| First tank | $5.9 \times 10^6$ | $6.4 \times 10^6$ | $5.5 \times 10^6$ |
| Second tank | 0 | $0.8 \times 10^6$ | $1.0 \times 10^6$ |
| | | | [unit, cells/ml] |

As is seen from Table 1, the cell density in the first tank was almost constant. This is because the cell count moved from the first tank into the second tank via the septum was substantially equal to the cell count increased by cell growth in the first tank. In this case, a flow rate of the septum-passing medium per unit area was 75 ml/cm$^2$·day.

The cell size is about 10 $\mu$m and is larger than 5 $\mu$m of a nominal pore size of the SUS316L-made woven cloth-like material. However, since cells are deformable, it is considered that when the septum passing medium flow rate per unit area is large, they would be deformed sufficiently to pass through the septum.

The foregoing results reveal that where JTC-1 strain cells were cultured using the SUS316L-made woven cloth-like septum having a pore size of 5 $\mu$m, and it was possible to increase the cell count in the first tank when the septum-passing medium flow rate per unit area was set to below 75 ml/cm$^2$·days.

EXAMPLE 2

Cells were cultured using the apparatus shown in FIG. 1, while supplementing medium to the inner tank portion (corresponding to the first zone) through medium-feeding pipe 124.

A septum having the whole volume of 3.0 liters and composed of SUS316L-made woven cloth-like material described above having a cylindrical wall closed at the bottom was disposed as shown in FIG. 1.

A modified stirring element immersed in the inner tank portion was rotated by a motor. A magnet stirrer 110 was put on the bottom of the outer tank portion (corresponding to the second zone) and rotated with a stirrer. The rotation speed of the stirring element was set at 100 rpm and the rotation speed of the magnetic stirrer was set at 180 rpm.

Using the same medium as in Example 1, the medium was added to have a medium volume of 2.5 liters in the inner tank portion and to have a medium volume of 2.7 liters in the outer tank portion. The effective area of the septum was 800 $cm^2$ in this case. JTC-1 strain cells were inoculated on the medium in the inner tank portion and became $1.2 \times 10^6$ cells/ml. Using a peristaltic pump, the medium was supplemented into the inner tank portion. While controlling the liquid surface on a constant level, the medium was withdrawn from the outer tank portion. A flow amount of the medium supplemented to the inner tank portion was 2.7 to 6.3 $ml/cm^2 \cdot day$ when expressed by the septum-passing medium flow rate per unit area. Reverse wash of the septum was not performed at all over the whole period of culturing.

A temperature for culturing was 37° C. Control of the dissolved oxygen concentration and pH was made by the liquid surface blowing method. The dissolved oxygen concentration and pH were set at 2 ppm and 7.2, respectively, by regulating flow amounts of air, oxygen and carbon dioxide.

Figure 5:
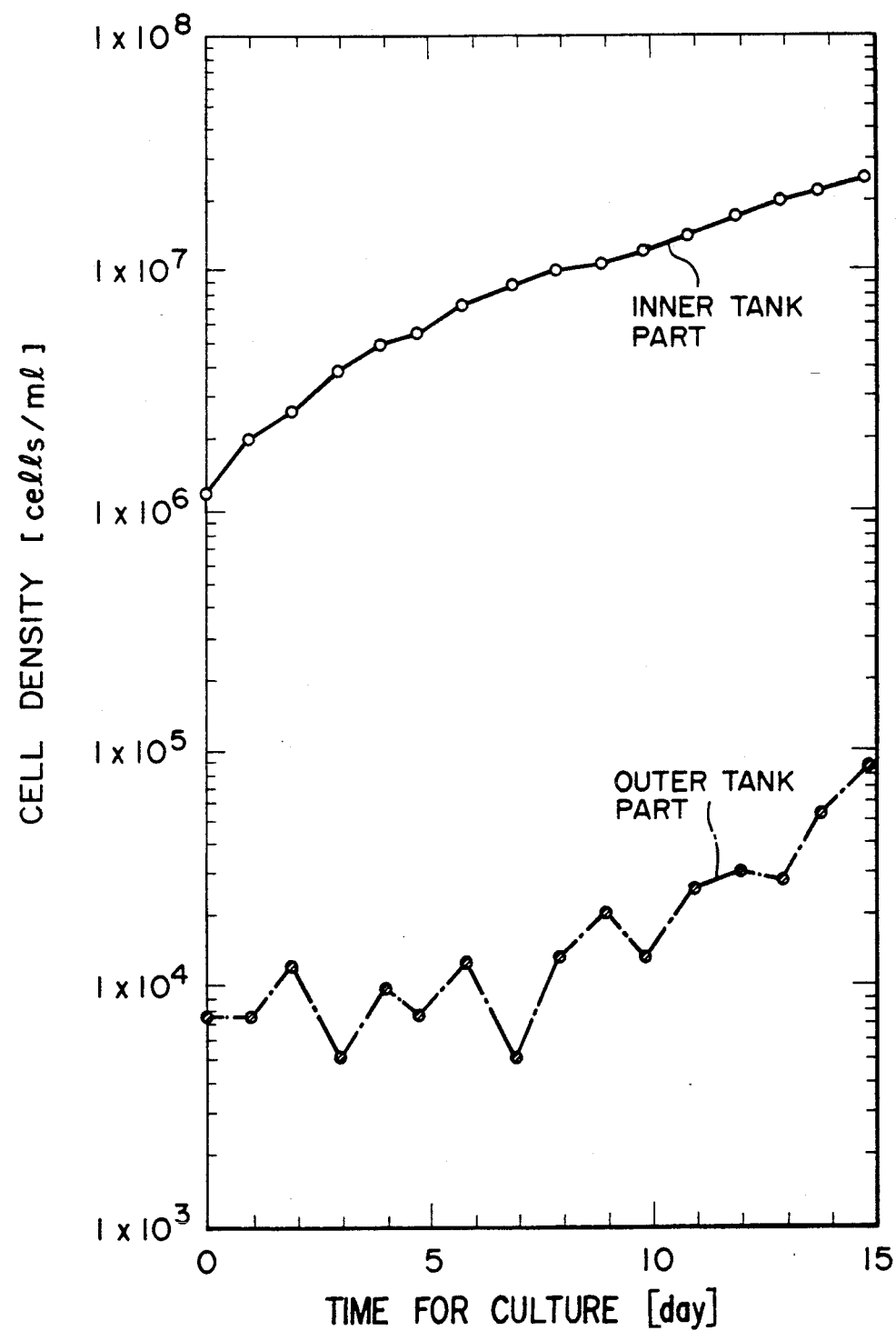
FIG. 5 is a graph showing change of cell density in Example 2 with passage of time.

Change of cell densities in the inner tank portion and in the outer tank portion with passage of time is shown in FIG. 5, wherein the solid line shows the change of cell density in the inner tank portion and the single-dotted chain line shows the change in the outer tank portion. The cell density in the inner tank portion reached $2.5 \times 10^7$ cells/ml on Day 15 after initiation of the incubation and a cell survival rate at this time was 91%; and, the cell density in the inner tank portion reached $8.5 \times 10^4$ cells/ml. Since the cell density in the outer tank portion was 1/300 time that of the inner tank portion, the cell count passed through the septum and flown out of the culture system is in a negligible range.

By the above results, it was confirmed that cell culture at a high density can be readily achieved in a large scale, using the culture tank of the present invention.

EXAMPLE 3

Using the apparatus shown in FIG. 1, cells were cultured while supplementing medium to the inner tank portion (corresponding to the first zone) through medium-feeding pipe 124 to examine clogging in the SUS316L-made woven cloth-like material described above and recovery by reverse washing.

A septum having the whole volume of 0.7 liter and composed of SUS316L-made woven cloth-like material described above having a cylindrical wall closed at the bottom was disposed in a glass-made culture tank having the whole volume of 1.7 liter, as shown in FIG. 1.

A modified stirring element immersed in the inner tank portion was rotated from the upper part by a motor. A magnet stirrer was put on the bottom of the outer tank portion (corresponding to the second zone) and rotated with a stirrer. The rotation speed of the stirring element was set at 100 rpm and the rotation speed of the magnetic stirrer was set at 250 rpm.

Using the same medium as in Example 1, the medium was added to have a medium volume of 0.5 liter in the inner tank portion and to have a medium volume of 0.23 liter in the outer tank portion. The effective area of the septum was 220 $cm^2$ in this case. JTC-1 strain cells were inoculated on the medium in the inner tank portion. Using a peristaltic pump, the medium was supplemented into the inner tank portion. While controlling the liquid surface on a constant level, the medium was withdrawn from the outer tank portion. A flow amount of the medium supplemented to the inner tank portion was 4.7 to 12.8 $ml/cm^2 \cdot day$, when expressed by the septum-passing medium flow rate per unit area.

A temperature for culturing was 37° C. Control of the dissolved oxygen concentration and pH was made by the liquid surface blowing method using a spurger. The dissolved oxygen concentration and pH were set at 2 ppm and 7.2, respectively, by regulating flow amounts of air, oxygen and carbon dioxide.

When cells were cultured up to Day 28 after initiation of the incubation, clogging of the septum occurred to some extent. In this case, the maximum medium flow amount per unit time in which liquid level did not change in the inner tank portion, namely, the maximum flow rate of the septum through which the liquid could pass was 5.1 $ml/cm^2 \cdot day$. At this time, 100 ml of the medium was rapidly added to the outer tank portion and reverse wash was performed by a hydrostatic pressure difference in the liquid surface between the inner and outer tank portions at a flow rate of 160 $ml/cm^2 \cdot day$ for 4 minutes. By doing so, the maximum flow rate of the septum through which the liquid could pass was recovered to 6.1 $ml/cm^2 \cdot day$. Again 180 ml of the medium was rapidly added to the outer tank portion on Day 31 after initiation of the incubation and reverse wash was performed at a flow rate of 170 $ml/cm^2 \cdot day$ for 7 minutes. The maximum flow rate of the septum through which the liquid could pass was further recovered to 7.0 $ml/cm^2 \cdot day$. This reverse wash was carried out every 3 other days, whereby cell culture could be performed for further one month.

The foregoing results reveal that even though a flow rate of the medium becomes small which could pass through the septum occurred due to clogging, it was possible to remove the clogging and recover the septum by reverse wash in a simple operation and the thus recovered state could be maintained for several days.

EXAMPLE 4

Using the twin tapping flask, diffusion coefficients of glucose (nutrient) and lactic acid (wastes) were determined by measurement with respect to the SUS316L-made woven cloth-like material and semi-permeable membrane.

A septum having an effective area of 2.1 $cm^2$ comprising the SUS316L-made woven cloth-like material described above was disposed in the twin tapping flask. To the first tank was added 80 ml of glucose-free DM-160AU medium (supplemented with 10% newborn bovine, 0.3 g/l of glutamine and 0.1 g/l of kanamycin) supplemented with 0.5 g/l of lactic acid. To the second tank was added 80 ml of DM-160AU medium (supplemented with 10% newborn bovine serum, 0.3 g/l of glutamine and 0.1 g/l of kanamycin). The DM-160AU medium was prepared to contain 1.0 g/l of glucose. A rotation speed of the stirrer was set at 400 rpm and a culture temperature was set at 37° C. Concentrations of glucose and lactic acid in the first tank and the second tank were measured every two other hours.

Next, a septum having an effective area of 1.5 cm$^2$ comprising a semi-permeable membrane having a fractional molecular weight of 30000 and a thickness of 200 μm was disposed in the twin tapping flask. To the first tank was added 80 ml of glucose-free DM-160AU medium (supplemented with 10% newborn bovine serum, 0.3 g/l of glutamine and 0.1 g/l of kanamycin) supplemented with 0.5 g/l of lactic acid. To the second tank was added 80 ml of DM-160AU medium (supplemented with 10% newborn bovine serum, 0.3 g/l of glutamine and 0.1 g/l of kanamycin). The DM-160AU medium was prepared to contain 1.0 g/l of glucose. A rotation speed of the stirrer was set at 400 rpm and a culture temperature was set at 37° C. Concentrations of glucose and lactic acid in the first tank and the second tank were measured every two other hours.

Diffusion coefficients of glucose and lactic acid in the SUS316L-made woven cloth-like material and the semi-permeable membrane in the first tank and the second tank were determined. The results are shown in Table 2.

TABLE 2

| Material | Diffusion Coefficient of Glucose | Diffusion Coefficient of Lactic Acid |
|---|---|---|
| SUS316L-made woven cloth-like material | $9.3 \times 10^{-6}$ | $9.3 \times 10^{-6}$ |
| Semi-permeable membrane | $8.8 \times 10^{-7}$ | $1.3 \times 10^{-6}$ |

[unit, cm$^2$/s]

As is seen from Table 2, the diffusion coefficients of glucose and lactic acid in the SUS316L-made woven cloth-like material were larger by 11 times and 7 times, respectively, than the diffusion coefficients of glucose and lactic acid in the semi-permeable membrane.

EXAMPLE 5

Cells were cultured using the apparatus shown in FIG. 1, while supplementing medium to the outer tank portion (corresponding to the second zone) through medium-feeding pipe 106.

A septum having the whole volume of 3.0 liters and composed of SUS316L-made woven cloth-like material described above having a cylindrical wall closed at the bottom was disposed in a glass-made culture tank having the whole volume of 8.0 liters, as shown in FIG. 1. Four pressure equalization ports each having a size of 15 mmφ were provided in a septum flange. By the pressure equalization ports, a pressure difference between the inner tank portion and the outer tank portion is kept at substantially zero.

A modified stirring element immersed in the inner tank portion was rotated from the upper part by a motor. A magnet stirrer was put on the bottom of the outer tank portion (corresponding to the second zone) and rotated with a stirrer. The rotation speed of the stirring element was set at 100 rpm and the rotation speed of the magnetic stirrer was set at 180 rpm.

Using the same medium as in Example 1, the medium was added to have a medium volume of 2.5 liters in the inner tank portion and to have a medium volume of 2.7 liters in the outer tank portion. The effective area of the septum was 800 cm$^2$ in this case. JTC-1 strain cells were inoculated on the medium in the inner tank portion and became $4 \times 10^5$ cells/ml. Using a peristaltic pump, the medium was supplemented into the inner tank portion. While controlling the liquid surface on a constant level, the medium was withdrawn from the outer tank portion. A flow amount of the medium supplemented to the inner tank portion was 1.2 to 6.7 ml/cm$^2$·day when expressed by the septum-passing medium flow rate per unit area.

A temperature for culturing was 37° C. Control of the dissolved oxygen concentration and pH was made by the liquid surface blowing method using a spurger. The dissolved oxygen concentration and pH were set at 2 ppm and 7.2, respectively, by regulating flow amounts of air, oxygen and carbon dioxide.

Figure 6:
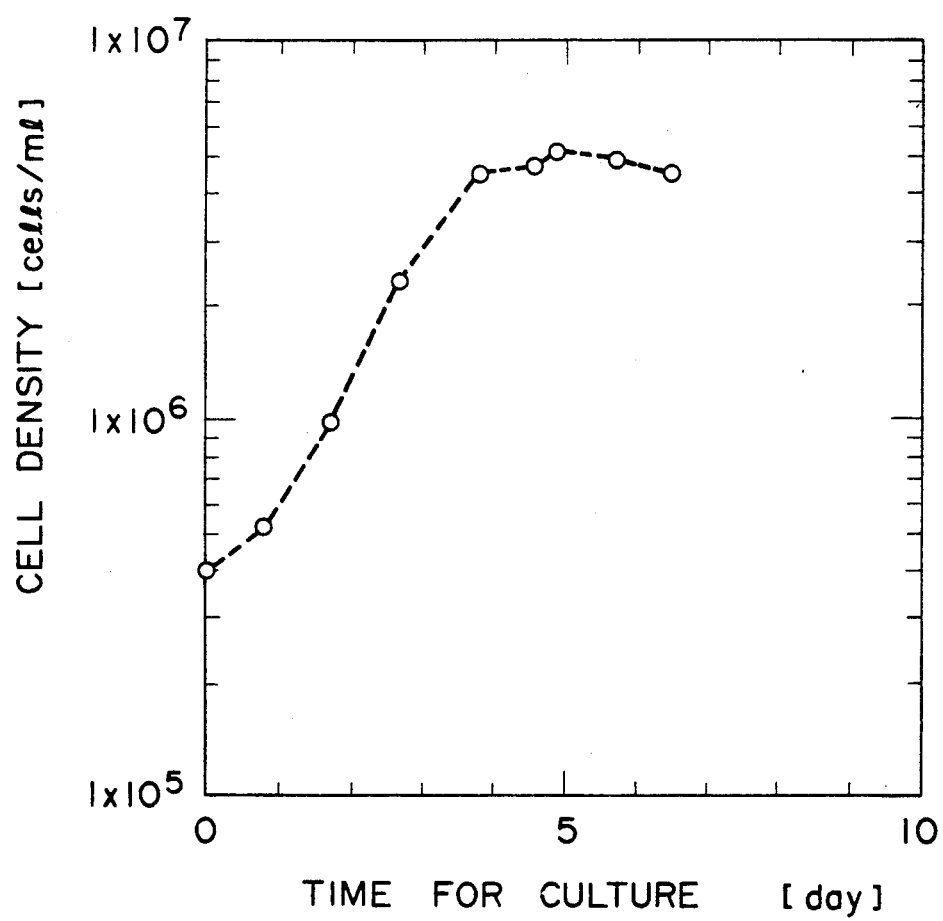
FIG. 6 is a graph showing change of cell density in Example 5 with passage of time.

Change of cell density in the inner tank portion is shown in FIG. 6. The cell density at this stage reached $5.2 \times 10^6$ cells/ml on Day 5 after initiation of the incubation and a cell survival rate at this time was 96%. Furthermore, run-off of the cells out of the outer tank portion was not noted over the entire period during the incubation.

By the above results, it was confirmed that cell culture at such a high cell density as on $5 \times 10^6$ cells/ml level can be readily achieved in a large scale, when using the culture tank of the present invention.

Comparative Example 1

In order to compare to Example 5, cells were cultured using the same apparatus, process, medium and seed cells as in Example 5, using a semi-permeable membrane as the septum.

A septum comprising a semi-permeable membrane having a fractional molecular weight of 30000 and a thickness of 200 μm was disposed in a glass-made culture tank having the whole volume of 8.0 liters, as shown in FIG. 1. Four pressure equalization ports each having a size of 15 mmφ were provided in a septum flange. By the pressure equalization ports, a pressure difference between the inner tank portion and the outer tank portion is kept at substantially zero.

Using the same medium as in Example 1, the medium was added to have a medium volume of 2.5 liters in the inner tank portion and to have a medium volume of 2.7 liters in the outer tank portion. The effective area of the septum was 800 cm$^2$ in this case. JTC-1 strain cells were inoculated on the medium in the inner tank portion and became $4 \times 10^5$ cells/ml. Using a peristaltic pump, the medium was supplemented into the inner tank portion. While controlling the liquid surface on a constant level, the medium was withdrawn from the outer tank portion. A flow amount of the medium supplemented to the inner tank portion was 1.2 to 6.7 ml/cm$^2$·day when expressed by the septum-passing medium flow rate per unit area.

A temperature for culturing was 37° C. Control of the dissolved oxygen concentration and pH was made by the liquid surface blowing method using a spurger. The dissolved oxygen concentration and pH were set at 2 ppm and 7.2, respectively, by regulating flow amounts of air, oxygen and carbon dioxide.

Figure 7:
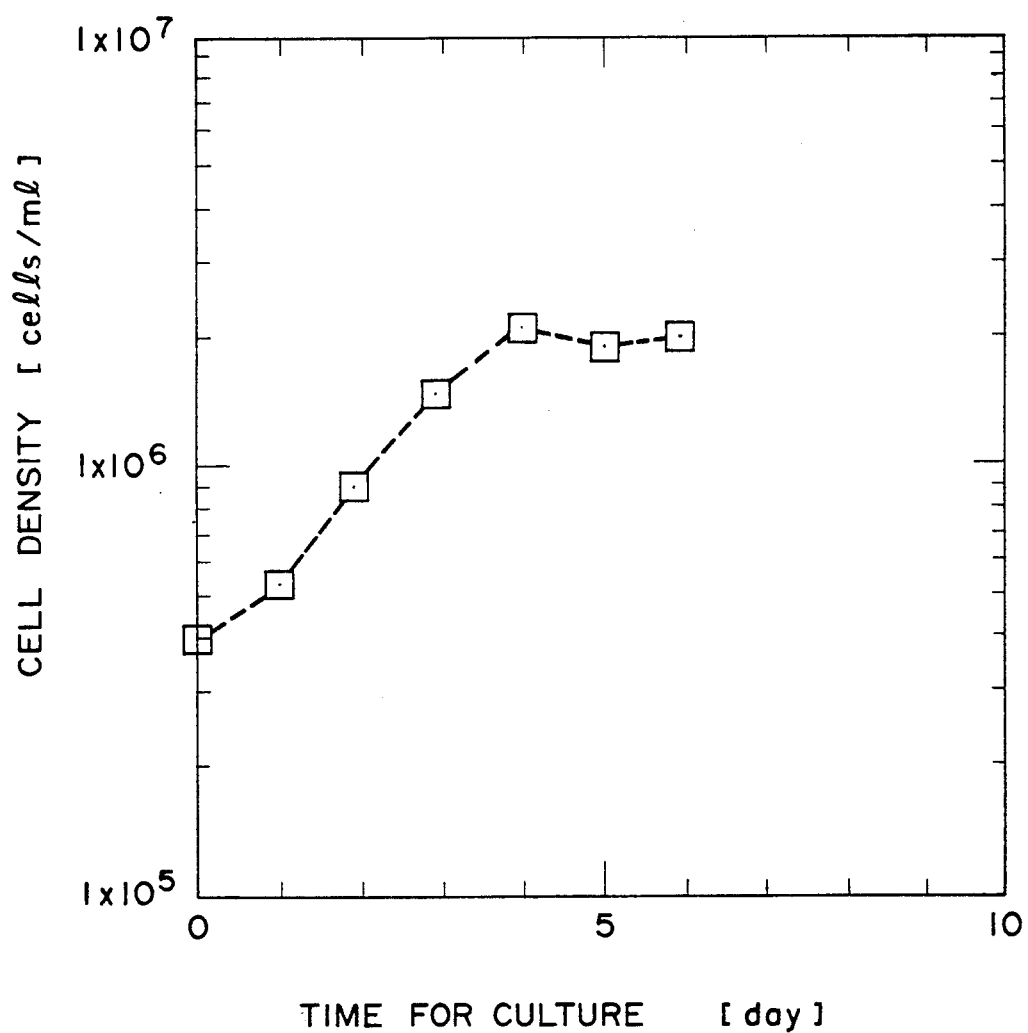
FIG. 7 is a graph showing change of cell density in Comparative Example 1 with passage of time.

Change of cell density in the inner tank portion is shown in FIG. 7. The cell density at this stage reached $2.1 \times 10^6$ cells/ml on Day 4 after initiation of the incubation but the cells did not grow any more. Furthermore, run-off of the cells out of the outer tank portion was not noted over the entire period during the incubation.

By the above results, it was confirmed that cell culture at a high cell density was difficult in the case of using the semi-permeable membrane as the septum.

As is clear from the foregoing, the supply of nutrients and the removal of wastes can be stably made continuously over long periods of time without any cell disruption according to the present invention. Therefore, cell culture at a high cell density can be achieved in a large scale.

What is claimed is:

1. A method of culturing cells suspended in a liquid medium comprising the steps of:
   placing cells to be cultured which are suspended in the liquid medium in a first zone;
   continuously supplying the liquid medium to said first zone;
   providing a second zone which is separated from said first zone by a septum which has pores having the size that allows the cultured cells and the liquid medium to permeate therethrough from said first zone to said second zone, but resist against the cells passing freely therethrough;
   continuously withdrawing from said second zone, the liquid medium that has passed through said pores of said septum from said first zone to said second zone to proliferate cell growth in said first zone; and
   controlling the flow rate of liquid medium supplied to said first zone to control the number of cells passing through said pores of said septum from said first zone in said second zone, so that the number of cells passing through from said first zone to said second zone does not exceed the number of cells increased by cell growth in said first zone.

2. A method of culturing cells according to claim 1, wherein said septum is composed of a woven cloth-like material.

3. A method of culturing cells according to claim 2, wherein said septum has pores substantially having a size of approximately 5 $\mu$m.

4. A method of culturing cells suspended in a liquid medium comprising the steps of:
   a) placing cells to be cultured which are suspended in the liquid medium in a first zone;
   b) continuously supplying the liquid medium along with nutrients to said first zone;
   c) providing a second zone which is separated from said first zone by a septum which has pores having the size that allows the cultured cells and the liquid medium to permeate therethrough from said first zone to said second zone, but resist against the cells passing freely therethrough;
   d) continuously withdrawing from said second zone the liquid medium that has passed through said pores of said septum from said first zone to said second zone to proliferate cell growth in said first zone;
   e) controlling the flow rate of liquid medium supplied to said first zone to control the number of cells passing through said pores of said septum from said first zone to said second zone, so that the number of cells passing through from said first zone to said second zone does not exceed the number of cells increased by cell growth in said first zone; and
   f) after a predetermined time interval, stopping the supply of liquid medium to said first zone and stopping the withdraw of liquid medium from said second zone, and supplying the liquid medium to said second zone for a shorter time period than said predetermined time interval, to reverse the flow of liquid medium, to cause flow from said second zone to said first zone, stopping the supply of liquid medium to said second zone, and supplying, withdrawing and controlling the liquid medium as received in steps b)–e).

5. A method of culturing cells suspended in a liquid medium comprising the steps of:
   providing cells to be cultured which are suspended in the liquid medium in a first zone;
   providing a second zone which is separated from said first zone by a septum which has pores having the size that allows the liquid medium, including nutrients, cell wastes and cell products contained in the liquid medium to pass therethrough between said first zone and said second zone, but resists against the cell passing therethrough;
   continuously supplying the liquid medium to said second zone from one region of said second zone;
   continuously withdrawing from another region of said second zone, the liquid medium with the cell wastes and products that has passed through said pores of said septum from said first zone to said second zone; and
   controlling the flow rate of the supply of liquid medium to said second zone so that the nutrients in the liquid medium are supplied to the cells by diffusion from said second zone to said first zone and the cell wastes and products are moved by diffusion from the first zone to said second zone to proliferate cell growth in said first zone.

6. A method of culturing cells according to claim 5, wherein said septum is composed of a material having an electrostatic charge of the same polarity as that of the electrostatic charge possessed by the cells suspended in said first zone, wherein the same polarity causes the cells to repel away from the septum to prevent the cells from passing through said pores from said first zone to said second zone.

7. A method of culturing cells according to claim 5, wherein said septum is electrically charged to provide an electrostatic charge of the same polarity as that of the electrostatic charge possessed by the cells suspended in said first zone, wherein the same polarity causes the cells to repel away from the septum to prevent the cells from passing through said pores from said first zone to said second zone.

8. An apparatus for culturing cells suspended in a liquid medium comprising:
   first means for containing cells to be cultured which are suspended in the liquid medium;
   second means for containing at least the liquid medium;
   a septum means having pores, wherein said pores have the size that allows the cultured cells and the liquid medium along with nutrients, cell waste and cell products to permeate therethrough, but resists against the cells freely passing therethrough,
   wherein said first means and second means being separated from each other by said septum means, wherein the cells suspended in the liquid medium in said first means can pass through said pores between said first means and said second means;
   means for continuously supplying the liquid medium along with nutrients into said first means to supply the nutrients to the cells to proliferate cell growth in said first means;
   means for continuously withdrawing from said second means, the liquid medium along with the cell and the cell wastes and products suspended in the liquid medium which has flowed into said second means through the pores of said septum means; and means for controlling the flow rate of liquid medium supplied to said first means to control the number of cells passing through said pores of said septum from said first means to said second means, so that the number of cells passing through from said first means to said second means does not exceed the number of cells increased by cell growth in said first means.

9. An apparatus for culturing cells according to claim 8, wherein said septum means is composed of a woven cloth-like material.

10. An apparatus for culturing cells suspended in a liquid medium comprising:

first means for containing cells to be cultured which are suspended in the liquid medium;

second means for containing at least the liquid medium;

a septum means having pores, wherein said pores have the size that allows the cultured cells and the liquid medium along with cell wastes and cell products to permeate therethrough, but resists against the cells passing therethrough, wherein said first means and second means being separated from each other by said septum means, wherein the cells suspended in the liquid medium in said first means can pass through said pores between said first means and said second means;

means for continuously supplying the liquid medium along with nutrients into said first means to supply nutrients to the cells to proliferate cell growth in said first means;

means for continuously withdrawing from said second means, the liquid medium along with the cells and the cell wastes and products which has flowed into said second means through the pores of said septum means;

means for controlling the flow rate of liquid medium supplied to said first means to control the number of cells passing through said pores of said septum from said first means to said second means, so that the number of cells passing through from said first means to said second means does not exceed the number of cells increased by cell growth in said first means; and means for controlling the supply of liquid medium to said first means by stopping the supply of liquid medium to said first means and stopping the withdraw of liquid medium from said second means after a predetermined time interval, and supplying the liquid medium to said second means for a shorter period than said predetermined time interval to reverse the flow of liquid medium, to cause flow from said second means to said first means, and stopping the supply of said liquid medium to said second means, and supplying the liquid medium to said first means and withdrawing the liquid medium from said second means for said predetermined time interval.

11. An apparatus for culturing cells suspended in a liquid medium comprising:

first means for containing cells to be cultured which are suspended in the liquid medium;

second means for containing at least the liquid medium;

a septum means having pores, wherein said pores have the size that allows the liquid medium to permeate therethrough, but resists against the cells passing therethrough, wherein said first means and second means being separated from each other by said septum means, wherein nutrients, cell wastes, and cell products in the liquid medium can pass through said pores between said first means and said second means;

means for continuously supplying the liquid medium into one region of said second means to supply nutrients to the cells in said first means through the pores of said septum means to cells to proliferate cell growth in said first means; and means for continuously withdrawing from another region of said second means, the liquid medium along with the cell wastes and products that has flowed into the second means through the pores of said septum means, wherein the flow rate of the supply of liquid medium to said first means is controlled so that the nutrients for the cells in the liquid medium are supplied to the cells in the first means by diffusion from said second means to said first means and the cell wastes and products are removed from said first means by diffusion to said second means to proliferate cell growth in said first means.

12. An apparatus for culturing cells according to claim 11, wherein said septum means is composed of a material having an electrostatic charge of the same polarity as that of the electrostatic charge possessed by the cells suspended in said first means, wherein the same polarity causes the cells to repel away from the septum means to prevent the cells passing through said pores.

13. An apparatus for culturing cells according to claim 11, wherein said septum means is electrically charged to provide an electrostatic charge of the same polarity as that of the electrostatic charge possessed by the cells suspended in said first means, wherein the same polarity causes the cells to repel away from the septum means to prevent the cells passing through said pores.

14. An apparatus for culturing cells according to claim 11, wherein said second means surrounds said first means and said septum means forms said first means, and said one region and said another region of said second means are located furthest from each other.

15. An apparatus for culturing cells suspended in a liquid medium comprising:

first means for containing cells to be cultured which are suspended in the liquid medium;

second means for containing at least the liquid medium;

a septum means having pores, wherein said pores have the size that allows the cultured cells and the liquid medium to permeate therethrough, but resists against the cell passing freely therethrough, wherein said first means and second means being separated from each other by said septum means, wherein the cells suspended in the liquid medium in said first means communicate between said first means and said second means via said pores;

means for continuously supplying the liquid medium into said first means to supply nutrient to the cells to proliferate cell growth in said first means;

means for continuously withdrawing from said second means, the liquid medium that has flowed into the second means through the pores of said septum means;

means for controlling the flow rate of liquid medium supplied to said first means to control the number of cells passing through said pores of said septum from said first means to said second means, so that the number of cells passing through from said first means to said second means does not exceed the number of cells increased by cell growth in said first means;

means for detecting the level of liquid medium in said first means; and means for reversibly controlling the flow of liquid medium from said second means to said first means upon detection of a predetermined level in said first means by stopping the supply of liquid medium to said first means and then supplying the liquid medium to said second means for a predetermined time interval to permit flow of the liquid medium from said second means to said first means, and then stopping the supply of liquid medium to said second means and supplying the liquid medium to said first means and withdrawing the liquid medium from said second means.

* * * * *